United States Patent
Dam et al.

(10) Patent No.: US 9,162,960 B2
(45) Date of Patent: Oct. 20, 2015

(54) PROCESS FOR THE PREPARATION OF A BENZENE DERIVATIVE

(71) Applicants: Furanix Technologies B.V., Amsterdam (NL); Stichting Dienst Landbouwkunding Onderzoek, Wageningen (NL)

(72) Inventors: Matheus Adrianus Dam, Amsterdam (NL); Edserd de Jong, Amsterdam (NL); Jacco van Haveren, Ede (NL); Aliaksei Pukin, Zwijndrecht (NL)

(73) Assignee: Furanix Technologies B.V., Amsterdam (NL)

( * ) Notice: Subject to any disclaimer, the term of this patent is extended or adjusted under 35 U.S.C. 154(b) by 0 days.

(21) Appl. No.: 14/346,380

(22) PCT Filed: Sep. 28, 2012

(86) PCT No.: PCT/NL2012/050680
§ 371 (c)(1),
(2) Date: Mar. 21, 2014

(87) PCT Pub. No.: WO2013/048248
PCT Pub. Date: Apr. 4, 2013

(65) Prior Publication Data
US 2014/0235892 A1    Aug. 21, 2014

Related U.S. Application Data

(60) Provisional application No. 61/541,573, filed on Sep. 30, 2011.

(30) Foreign Application Priority Data

Sep. 30, 2011   (NL) ...................................... 2007509

(51) Int. Cl.
| | |
|---|---|
| C07C 51/16 | (2006.01) |
| C07C 51/41 | (2006.01) |
| C07C 51/285 | (2006.01) |
| C07D 493/18 | (2006.01) |
| C07C 51/275 | (2006.01) |
| C07D 307/42 | (2006.01) |

(52) U.S. Cl.
CPC ................ C07C 51/41 (2013.01); C07C 51/16 (2013.01); C07C 51/275 (2013.01); C07C 51/285 (2013.01); C07C 51/412 (2013.01); C07D 307/42 (2013.01); C07D 493/18 (2013.01)

(58) Field of Classification Search
CPC .................................. C07C 51/16; C07C 51/41
See application file for complete search history.

(56) References Cited

U.S. PATENT DOCUMENTS

| | | | |
|---|---|---|---|
| 2,405,267 | A | 8/1946 | Nudenberg |
| 2,729,674 | A | 1/1956 | McKinnis |
| 4,138,354 | A | 2/1979 | Sochol et al. |
| 7,385,081 | B1 | 6/2008 | Gong |
| 2010/0127220 | A1 | 5/2010 | Tierney et al. |
| 2010/0331568 | A1 | 12/2010 | Brandvold |
| 2011/0144359 | A1 | 6/2011 | Heide et al. |

FOREIGN PATENT DOCUMENTS

| | | |
|---|---|---|
| EP | 2128227 A1 | 12/2009 |
| EP | 2197863 B1 | 11/2012 |
| GB | 1402705 | 8/1975 |
| WO | 2007104514 A2 | 9/2007 |
| WO | 2007136640 A2 | 11/2007 |
| WO | 2008128618 A1 | 10/2008 |
| WO | 2010151346 A1 | 12/2010 |

OTHER PUBLICATIONS

Pelter et al. J. Chem. Soc. Perkin Trans. 1, 1983, 1383-1386.*

(Continued)

*Primary Examiner* — Yong Chu
*Assistant Examiner* — Ana Z Muresan
(74) *Attorney, Agent, or Firm* — Hoffman & Baron, LLP

(57) ABSTRACT

A substituted benzene derivative is prepared in a process, which includes reacting a furan derivative of formula (I):

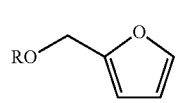

(I)

wherein R is an alkyl group,
with an olefin of formula (II):

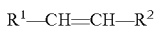

$R^1$—CH═CH—$R^2$    (II)

wherein $R^1$ and $R^2$ are the same or different and independently are selected from the group consisting of hydrogen, —CN, —CHO and —COOR³, wherein $R^3$ is selected from hydrogen or an alkyl group, or $R^1$ and $R^2$ together form a —C(O)—O—(O)C— group, with the proviso that $R^1$ and $R^2$ are not both hydrogen,
to produce a bicyclic ether; and dehydrating the bicyclic ether to obtain a benzene derivative.
The benzene derivative thus obtained can suitably be converted to a benzene carboxylic acid compound by oxidation.

20 Claims, No Drawings

(56) References Cited

OTHER PUBLICATIONS

Theurillat-Moritz, Viviane, et al., "Synthesis of Enantiomerically Pure 7-Oxabicyclo[2.2.1]hept-2-enes Precursors in the Preparation of Taxol Analogues", Tetrahedron Assemmetry, vol. 7, No. 11, pp. 3163-3168, 1996.

Metral, Jean-Luc, et al., "133. Diels-Ahier Regioselectivity Controlled by Remote Substituents. The Cycloadditions of 1-(Dimethoxymethyl)2,3-dimethylidene-and-2,3,5,6-detramethylidene-7-oxabicyclo[2.2.1 heptanes)", Helvetica Chimica Acta—vol. 69 (1986), p. 1287.

* cited by examiner

PROCESS FOR THE PREPARATION OF A BENZENE DERIVATIVE

CROSS-REFERENCE TO RELATED APPLICATIONS

This application is the National Stage of International Application No. PCT/NL2012/050680 filed Sep. 28, 2012, which claims the benefit of Netherlands Application No. 2007509, filed Sep. 30, 2011, and of U.S. Provisional Application No. 61/541,573, filed Sep. 30, 2011, the contents of all of which are incorporated by reference herein.

FIELD OF THE INVENTION

The present invention relates to a process for the preparation of a benzene derivative, more in particular, to a process for the preparation of a benzene derivative obtained via a Diels-Alder reaction of a furan derivative with a substituted olefin.

BACKGROUND OF THE INVENTION

In recent times a tendency has grown to obtain a variety of chemicals from renewable resources. In this context there has been a tendency to create chemicals from biomass carbohydrates, such as cellulose, starch, hemicellulose, sugars and the like. Under dehydration conditions these carbohydrates can be converted into a number of interesting chemicals, including levulinic acid, furfural, hydroxymethyl furfural and derivatives thereof. It would be of interest to use these chemicals for the production of value-added chemical compounds. Examples of such value added chemical compounds include phthalic acid, terephthalic acid, isophthalic acid, trimellitic acid, hemimellitic acid, pyromellitic acid and other benzene derivatives that contain two or more carboxylic moiety substituents.

The Diels-Alder reaction with furan derivatives is known. The Diels-Alder reaction of furan and ethylene to the desired product 3,6-epoxycyclohexene (7-oxabicyclo[2.2.1]hept-2-ene) has been described in U.S. Pat. No. 2,405,267. In an example 3,6-epoxycyclohexene was isolated (see formula A).

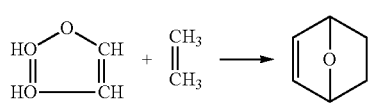

A

In GB 1402705 it is reported that the 3,6-epoxycyclohexene under the conditions of its formation reacts further as an olefin in the subsequent Diels-Alder reaction with furan, resulting again in an olefin (see formula B below; n=1), which can further react with furan to form a polyaddition compound with n=2-50:

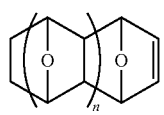

B

Furan was reported not to give self-addition if ethylene is not present.

In US 2010/0127220 a process for the preparation of pentacenes has been described, which process includes a process step wherein (i) dimethyl furan is reacted with maleic anhydride via a Diels-Alder reaction to yield a bicyclic ether. The bicyclic ether is subsequently dehydrated (ii) under aromatization conditions, thereby forming 4,7-dimethyl-isobenzofuran-1,3-dione (see process scheme C).

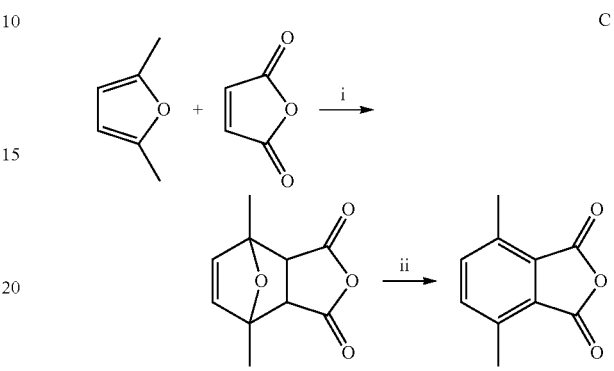

C

Although these processes include a Diels-Alder reaction with a furan derivative, the eventual product is not a benzene derivatives comprising carboxylic acid substituents.

Terephthalic acid is produced in a process according to U.S. Pat. No. 7,385,081. In this process 2,5-furan dicarboxylic acid is subjected to a Diels-Alder reaction with ethylene to yield a bicyclic ether, which subsequently is converted under aromatization conditions to terephthalic acid. The yields, however, are extremely low.

In WO 2010/151346 a catalytic process for the conversion of 2,5-dimethylfuran to p-xylene is described, wherein 2,5-dimethylfuran is reacted with ethylene under cycloaddition reaction conditions to produce p-xylene. The 2,5-dimethylfuran has been obtained from the conversion of glucose or fructose to 5-hydroxymethylfurfural, followed by the hydrogenation of 5-hydroxymethylfurfural to 2,5-dimethyl furan. This process has the drawback that hydrogenation of the hydroxymethyl and carbonyl functions of 5-hydroxymethyl furfural is followed by oxidation, which is a waste of resources. Moreover, the oxidation of the methyl groups in 2,5-dimethyl furan is relatively difficult.

SUMMARY OF THE INVENTION

The present invention is aimed at the production of benzene derivatives from renewable, oxygen-containing furfural compounds via a Diels-Alder reaction with an oxygen-containing olefin and the subsequent aromatization of the Diels-Alder products obtained. Accordingly, the present invention provides a process for the preparation of a substituted benzene derivative, which comprises
reacting a furan derivative of formula (I):

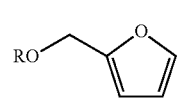

(I)

wherein R is an alkyl group,
with an olefin of formula (II):

$$R^1—CH=CH—R^2$$ (II)

wherein $R^1$ and $R^2$ are the same or different and independently are selected from the group consisting of hydrogen, —CN, —CHO and —COOR$^3$, wherein $R^3$ is selected from hydrogen or an alkyl group, or $R^1$ and $R^2$ together form a —C(O)—O—(O)C— group, with the proviso that $R^1$ and $R^2$ are not both hydrogen,
to produce a bicyclic ether; and
dehydrating the bicyclic ether.

DETAILED DESCRIPTION OF THE INVENTION

At dehydration of the bicyclic ether, aromatization occurs so that a benzene derivative is obtained that contains at least two or three substituents in a 1,2-, 1,3- or 1,2,3-substitution. The nature of these substituents allows for a relatively easy oxidation to desired compounds such as phthalic acid, isophthalic acid and hemimellitic acid (1,2,3-benzene tricarboxylic acid).

The oxidation of the alkoxymethyl substituent originating from the furan staring material and the optional aldehyde group originating from the olefin starting material is more flexible and easier than the oxidation of the methyl substituents (cf. WO 2010/151346), since the substituents are already partially oxidized. The oxidation is more selective if the alkyl group is not too big. Therefore the process is preferably conducted with a furan derivative wherein R is an alkyl group having from 1 to 6 carbon atoms, and more preferably is methyl or ethyl. The olefin that is used in the present process also comprises at least one oxygen atom already. Hence, the olefin also facilitates a subsequent oxidation. Suitable olefins are selected from the group consisting of acrolein, acrylic acid, acrylate alkyl esters, preferably wherein the alkyl moiety contains from 1 to 6 carbon atoms, maleic acid and maleic anhydride.

It is advantageous if the furan derivative that is being used as starting material can be directly derived from a biomass resource. Recently there has been work done on the conversion of carbohydrates to ethers and esters of 5-hydroxymethyl furfural. An example of such work is described in WO 2007/104514 as to the ethers of 5-hydroxymethyl furfural. In this patent application the conversion of a carbohydrate to the ether has been described wherein the carbohydrate is converted into the desired product in one step. Since it is advantageous to have the furan derivative of the present invention been made available via the most convenient method, the furan derivative used in the process of the present invention has preferably been derived from the dehydration of a carbohydrate. The carbohydrate is suitably selected from a pentose. A pentose is a monosaccharide with five carbon atoms, having the chemical formula $C_5H_{10}O_5$. They may either have an aldehyde functional group in position 1 (aldopentoses), or a ketone functional group in position 2 (ketopentoses). Suitable 5-carbon monosaccharides include but are not limited to arabinose, ribose, ribulose, xylose, xylulose and lyxose. The pentose may be recovered from the hydrolysis of pentose polymers pentosans, such a xylans and arabinosylans.

A suitable method for obtaining the desired furan starting material is to obtain furfural from the dehydration of a carbohydrate and to convert the furfural thus obtained to the desired starting material. Such conversion typically takes place via hydrogenation of the aldehyde group to a hydroxylic group and subsequent etherification of the hydroxylic group thus obtained. It is well known to obtain furfural from carbohydrate-containing biomass. A recent example thereof has been described in US 2011/0144359. Furfural may also be formed during the dehydration of a hexose.

The furan derivative used in the process of the present invention may be obtained from furfural by hydrogenation and etherification of the hydroxylic compound thus obtained with an alkanol, or by the decarbonylation of alkoxymethyl-furfural. The reaction of furfural with hydrogen in the presence of an alkyl alcohol and a catalyst system has been described in EP 2197863. The decarbonylation of alkoxymethyl furfural has been described in EP 2128227.

The Diels-Alder reaction of the furan derivative of formula (I) with the olefin of formula (II) can be carried out at under a broad variety of reaction conditions. Although elevated pressures may be applied, e.g., from 1 to 100 bar, more preferably, from 1 to 10 bar, it is most feasible to conduct the reaction at autogeneous pressure. The reaction temperature may also vary from far below 0° C. to elevated temperatures. Suitably, the reaction temperature varies from 0° C. to 150° C., preferably from 20 to 100° C.

Known Diels-Alder catalysts may also be used in the reaction. Suitable catalysts include Lewis acids, e.g., aluminium, boron, zinc, hafnium or iron compounds, such as $AlCl_3$, $Al(Et)Cl_2$, $Al(Et)_2Cl$, $BF_3$, $B(Ac)_3$, $ZnCl_2$, $ZnBr_2$, $Zn(Ac)_2$, $HfCl_4$, $FeCl_3$, $Fe(Ac)_3$, $FeCl_2$ and $Fe(Ac)_2$, but also halides of tin or titanium, such as $SnCl_4$ and $TiCl_4$. However, the reactants may be so reactive that a catalyst is not needed to make the reaction occur. Evidently, in such a case the skilled person may decide not to use a catalyst in view of economic considerations.

Although it is possible to conduct the present reaction between the furan derivative and the olefin in the presence of a solvent, it is preferred to refrain from employing a solvent. Nevertheless, in certain cases the use thereof may be convenient. The use of a solvent is convenient if the furan derivative and/or the bicyclic ether that is being produced is solid under the reaction conditions. The liquid phase thus obtained makes it easier to handle the reactant and/or the reaction products. Thereto, the solvent may be selected from a wide range of potential liquids. Suitably, the solvent is selected from the group consisting of alcohols, esters, ketones, amides, aldehydes, ethers, ionic liquids and sulphoxides. Advantageously, the solvents contain from 1 to 20 carbon atoms. Examples of alcohols include $C_1$-$C_6$ alcohols, in particular methanol, ethanol, n-propanol, isopropanol, butanol-1, butanol-2,2-methyl-propanol and tert-butanol. Suitable esters include the $C_1$-$C_{10}$ alkyl esters of $C_1$-$C_6$ carboxylic acids, such as methyl formate, methyl acetate, ethyl formate, ethyl acetate, methyl propionate, ethyl propionate, methyl butyrate, ethyl butyrate and ethylhexyl acetate. Suitable ketones contain 2 to 8 carbon atoms, such as acetone, butanone and methyl iso-butyl ketone. Suitable amides include acetamide and formamide, optionally substituted by one or two alkyl groups with 1 to 6 carbon atoms. Examples of suitable ethers include di($C_1$-$C_6$ alkyl) ethers, such as dimethyl ether, diethyl ether and methyl tert-butyl ether, and also cyclic ethers such as tetrahydrofuran. Suitable aldehydes include $C_1$-$C_6$ aldehydes, such as formaldehyde, acetaldehyde, propanal and hexanal. Suitable ionic liquids comprise a pyridinium or imidazolinium moiety. Examples include pyridinium chloride, 1-ethyl-3-methylimidazolium dicyanamide and 1-butyl-3,5-dimethylpyridinium bromide. A suitable sulphoxide is dimethylsulphoxide.

The relative amounts of the furan derivative of formula (I) and the olefin of formula (II) may vary. Since stoichiometry shows that one mole of furan may react with one mole of olefin, the molar ratio of the amount furan derivative to the amount of olefin generally will be about 1:1, although the person skilled in the art may decide to provide one of the reactants in excess to promote the reaction and/or to facilitate the complete conversion of the other reactant. Therefore, the molar ratio between the amount of furan derivative to the amount of olefin suitably ranges from 0.1:1 to 10:1, preferably from 0.5:1 to 2:1, most preferably about 1:1.

For the Diels-Alder reaction, the reactants may be added in a batch-wise or a continuous fashion. In a batch-wise fashion both the furan derivative and olefin are charged to a vessel, e.g. an autoclave, and made to react with each other. Typically one of the reactants may be added in portions, over a period of time, to the other reactant, e.g., by using a syringe as described in US 2010/0127220. If desired, the reaction mixture is maintained at a desired temperature for a period of time, e.g. whilst stifling to increase the yield of product. In a continuous fashion both a stream of furan derivative and a stream of olefin are fed to a reactor where they are contacted and from which reactor continuously a stream of product is withdrawn. The flow rate in a continuous reactor should be adapted such that the residence time is sufficient to allow a satisfactory conversion of the furan derivative and olefin. The Diels-Alder reaction is suitably carried out in a batch or continuous reactor wherein the residence time is from 0.1 to 72 hours, preferably from 0.5 to 48 hours.

After the Diels-Alder reaction, the bicyclic ether thus obtained may be isolated from the reaction product. However, it is preferred to dehydrate the bicyclic ether without isolation of the bicyclic ether from the reaction product. This would make the process simpler, without negatively affecting the resulting benzene derivative product or yield of the benzene derivative.

A solvent may also be present in the dehydration of the bicyclic ether. The solvent in which the dehydration is carried out may be the same as or different from the one wherein the Diels-Alder reaction is performed. If the Diels-Alder reaction is performed in the presence of a solvent, and if the dehydration is to take place in a different solvent, the former solvent may be removed via conventional ways, e.g., by distillation, and replaced by the latter solvent. If the same solvent is used in both the Diels-Alder reaction and the dehydration, the process is significantly simplified. Accordingly, the dehydration of the bicyclic ether is preferably performed in the presence of a solvent selected from the group consisting of alcohols, esters, ketones, amides, aldehydes, ethers, ionic liquids and sulphoxides. Suitable examples of the solvents are the same as those described above. Preferably, the solvent is an aliphatic alcohol containing 1 to 3 carbon atoms.

The dehydration reaction may be effected in a variety of ways. It is feasible to achieve dehydration by a thermal reaction; maintaining the bicyclic ether at temperatures of, e.g., from 20 to 100° C., would already result in a conversion into the envisaged benzene derivative. However, the bicyclic ether may be so reactive that the dehydration takes place at lower temperatures. This may especially be the case when the dehydration reaction is conducted in the presence of a catalyst. The catalyst can be selected from a homogeneous and a heterogeneous catalyst. The use of a homogeneous catalyst boils down to a process wherein the reaction is carried out in a homogeneous liquid phase and the catalyst is comprised in that liquid phase. When a heterogeneous catalyst is used, the reaction is conducted in a liquid reactant phase and a solid catalyst phase. The catalyst may be alkaline or acidic. Examples of acidic catalysts solid acid catalysts such as amorphous silica-alumina, zeolites, preferably zeolites in their H-form, and acidic ion exchange resins. Other suitable catalysts that may be dissolved in the appropriate solvent to yield a homogeneous catalysis environment, include organic and inorganic acids, such as alkane carboxylic acid, arene carboxylic acid, sulphuric acid, phosphoric acid, hydrochloric acid, hydrobromic acid and nitric acid. When an arene carboxylic acid is the eventually desired product, such as phthalic acid, isophthalic acid or hemimellitic acid, a preferred arene carboxylic acid is selected from phthalic acid, isophthalic acid and hemimellitic acid, since these acids provides catalytic activity and do not add an extraneous chemical to the reaction mixture.

Preferably, the catalyst is an alkaline catalyst. Suitable alkaline catalysts include hydroxides, alkanolates, carboxylates and carbonates. Advantageously, the cations in these alkaline catalysts are alkali metal, alkaline earth metal or ammonium ions. Preferably the cations are alkali metal ions, such as sodium or potassium ions. Suitable catalysts, therefore, include such as alkali metal methanolate, alkali metal ethanolate, alkali metal acetate, propionate or butyrate, and alkali metal carbonate or bicarbonate. Preferred are alkali metal methanolate and alkali metal ethanolate.

As indicated above, the bicyclic ether may be dehydrated thermally at temperatures ranging from 20 to 100° C. If a catalyst is used significantly lower temperatures are feasible. Advantageously, the bicyclic ether may be dehydrated at temperatures ranging from −20 to 100° C., preferably, from −5 to 90° C. The pressure at which the bicyclic ether is dehydrated is not critical. Most convenient is a pressure of about ambient, but the dehydration may also be performed at sub-atmospheric or super-atmospheric pressures. Suitably, the pressure at which the dehydration is conducted is in the range from 0.5 to 50 bar, preferably, from 1 to 10 bar.

The dehydration reaction may be conducted in a batch reactor and in a continuous reactor. The flow rate in a continuous reactor should be adapted such that the residence time is sufficient to allow a satisfactory conversion of the ether. The bicyclic ether is suitably dehydrated in a batch or continuous reactor wherein the residence time is from 0.1 to 48 hours, preferably from 0.1 to 4 hours.

As indicated above, the process according to the present invention is very suitable for providing an intermediate in the production of a benzene carboxylic acid. Therefore, the benzene derivative prepared by the process according to the invention may suitably be oxidized. Accordingly, the present invention further provides a process for the preparation of benzene carboxylic acid comprising preparing the benzene derivative prepared according to the process above and oxidizing the benzene derivative thus obtained. Accordingly the present invention provides a process for the preparation of a benzene carboxylic acid compound comprising reacting a furan derivative of formula (I):

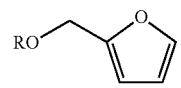

(I)

wherein R is an alkyl group,
with an olefin of formula (II):

$R^1$—CH=CH—$R^2$ (II)

wherein $R^1$ and $R^2$ are the same or different and independently are selected from the group consisting of hydrogen, —CN, —CHO and —COO$R^3$, wherein $R^3$ is selected from hydrogen or an alkyl group, or $R^1$ and $R^2$ together form a —C(O)—O—(O)C— group, with the proviso that $R^1$ and $R^2$ are not both hydrogen, to produce a bicyclic ether;

dehydrating the bicyclic ether to yield a benzene derivative; and oxidizing the benzene derivative thus obtained.

The benzene carboxylic acid compound thus obtained may suitably be the acid, a salt or an anhydride. The skilled person will realise that dependent on the nature of the substituents R, $R^1$, $R^2$ and $R^3$ the number of carboxylic acid groups on the benzene ring may vary from two to three.

The oxidation of the benzene derivative obtained may be effected in any conventional oxidation method, as will be appreciated by the skilled person. A suitable oxidation is effected by using an oxygen-containing gas in the presence of a catalyst that comprises cobalt and manganese. Aromatic carboxylic acids may suitably be prepared over a catalyst that contain bromine in addition to cobalt and manganese. Preparation of such a catalysts has, for instance, been described U.S. Pat. No. 4,138,354. The oxygen-containing gas may be air, oxygen-enriched air or substantially pure oxygen. However, other, more conventional and/or less expensive catalysts are also possible since the benzene derivatives obtained in the present process are more reactive and easier to oxidize than benzene derivatives that do not contain an oxygen atom in their substituents. Therefore, oxidation using potassium permanganate, nitric acid, or using oxygen over noble metal-containing catalyst (e.g., Rh, Pd) is also possible.

The temperature and pressure of the oxidation can be selected within wide ranges. The pressure of the reaction mixture is preferably between 5 and 100 bar, with a preference for pressures between 10 and 80 bar. In case the oxidant is an oxygen-containing gas, such as air, the gas can be continuously fed to and removed from the reactor, or all of the gas can be supplied at the start of the reaction. In the latter case, the pressure of the system will depend on the headspace volume and the amount of gas required to convert the starting material. It is clear that in the latter case, the pressure of the system may be significantly higher than when an oxygen-containing gas is continuously fed and removed.

The temperature of the reaction mixture is suitably between 60 and 220° C., preferably between 100 and 210° C., more preferably between 150 and 200° C., most preferably between 160 and 190° C.

In the preferred oxidation catalysts that comprise Co and Mn, molar ratios of cobalt to manganese (Co/Mn) are typically 1/1000-100/1, preferably 1/100-10/1 and more preferably 1/10-4/1.

Likewise, in these preferred oxidation catalysts, comprising also bromine, molar ratios of bromine to metals (e.g. Br/(Co+Mn)) are typically from 0.001 to 5.00, preferably 0.01 to 2.00 and more preferably 0.1 to 0.9.

Catalyst concentration (calculated on the metal, e.g., Co+Mn) is preferably between 0.1 and 10 mol % relative to the starting material, with a preference for loads between 2 and 6 mol %. Good results were obtained in general with catalyst loads of around 4 mol %.

Reaction times suitably range from 0.1 to 48 hours, preferably, from 0.5 to 24 hrs.

The skilled person will realise that the number of carboxylic groups on the benzene ring may be varied. He may vary this number by selecting the appropriate starting materials. Alternatively, he may want to decarboxylate the products, using a method similar to the one described in U.S. Pat. No. 2,729,674 for the mono-decarboxylation of trimellitic acid.

The invention will be further illustrated by means of the following examples.

EXAMPLE 1

1-Ethoxymethyl-7-oxabicyclo[2.2.1]hept-5-ene-2,3-dicarboxylic anhydride

Maleic anhydride, i.e. an olefin of formula (II) wherein $R^1$ and $R^2$ together form a —C(O)—O—(O)C— group, (8 mmol) was slowly added to furfuryl ethyl ether (8 mmol) at room temperature. The reaction mixture was stirred for 36 hours. The resulting yellow liquid was shown to consist of 96% of 1-ethoxymethyl-7-oxabicyclo[2.2.1]hept-5-ene-2,3-dicarboxylic anhydride.

EXAMPLE 2

3-(Ethoxymethyl)phthalic acid disodium salt

The product of Example 1, i.e., 1-ethoxymethyl-7-oxabicyclo[2.2.1]hept-5-ene-2,3-dicarboxylic anhydride (8 mmol) was, without purification, dissolved in methanol (10 ml). To this solution, solid sodium methoxide (0.86 g, 16 mmol) was added at 0° C. The resulting deep orange solution was stirred for 18 h at room temperature, after which the solvent was evaporated in vacuo. After drying for 1 h at 77° C. under reduced pressure, the solid was dissolved in water and heated under reflux for 5 h followed by treatment with charcoal (stirring for 30 min at reflux). Filtration and evaporation under reduced pressure yielded 3-(ethoxymethyl)phthalic acid disodium salt (37%).

EXAMPLE 3

Hemimellitic Acid 3-(Ethoxymethyl)phthalic acid disodium salt (3.7 mmol) from Example 2 was dissolved in water (40 ml). Potassium permanganate (7.5 mmol) was added and the resulting solution was stirred for 18 h at room temperature. The precipitate formed was filtered off and washed three times with hot water. The combined aqueous phase was evaporated under reduced pressure to approximately one third of the initial volume and cooled in an ice-bath. Concentrated HCl was added carefully for neutralization. The precipitated hemimellitic acid was collected on a glass filter, washed with water and dried (yield: 42%).

REFERENCE EXAMPLE 4

3-Methylphthalic acid disodium salt

2-Methyl furan was reacted with maleic anhydride in a manner similar to the procedure described in Example 1 to yield 1-methyl-7-oxabicyclo[2.2.1]hept-5-ene-2,3-dicarboxylic anhydride. An amount of 28 mmol of this compound was dissolved in methanol (50 ml). To this solution, solid sodium methoxide (56 mmol) was added at 0° C. The resulting deep orange solution was stirred for 18 h at room temperature, after which the solvent was evaporated in vacuo. After drying for 1 h at 77° C. under reduced pressure, the solid was dissolved in water and heated under reflux for 5 h followed by treatment with charcoal (stirring for 30 min at reflux). Filtration and evaporation under reduced pressure yielded 3-methylphthalic acid disodium salt (4.4 g, 71%).

REFERENCE EXAMPLE 5

Oxidation of 3-methyl phthalic acid

3-Methylphthalic acid disodium salt (4.4 mmol) was dissolved in water (50 ml). Potassium permanganate (14.7 mmol) was added and the resulting solution was stirred for 18 h at room temperature. A precipitate was formed. The precipitate was filtered off and washed three times with hot water. The combined aqueous phase was evaporated under reduced pressure to approximately one third of the initial volume and cooled in an ice-bath. Concentrated HCl was added carefully for neutralization. Expected precipitation of hemimellitic acid did not occur. After evaporation of water in vacuo, the dark residue represented a complex mixture of compounds.

From the comparison of the results of Example 3 and Reference Example 5, it is evident that the process according to the present invention provides advantageous results.

The invention claimed is:

1. A process for the preparation of a benzene carboxylic acid compound comprising:

reacting a furan of formula (I):

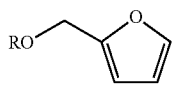 (I)

wherein R is an alkyl group,
with an olefin of formula (II):

 (II)

wherein $R^1$ and $R^2$ are the same or different and independently are selected from the group consisting of hydrogen, —CN, —CHO and —COOR$^3$, wherein $R^3$ is selected from hydrogen or an alkyl group, or $R^1$ and $R^2$ together form a —C(O)—O—(O)C— group, with the proviso that $R^1$ and $R^2$ are not both hydrogen,
to produce a bicyclic ether;
dehydrating the bicyclic ether in the presence of a catalyst at a temperature in the range from −5 to 90° C. to yield a substituted benzene; and
oxidizing the substituted benzene thus obtained, to yield the benzene carboxylic acid compound.

2. The process according to claim 1, wherein R is selected from an alkyl group containing from 1 to 6 carbon atoms.

3. The process according to claim 1, wherein the furan of formula (I) has been obtained from the dehydration of a carbohydrate to yield furfural and the conversion of furfural thus obtained.

4. The process according to claim 3, wherein the carbohydrate is selected from a pentose.

5. The process according to claim 3, wherein the carbohydrate is selected from arabinose, ribose, ribulose, xylose, xylulose and lyxose.

6. The process according to claim 1, wherein the furan of formula (I) has been obtained from the conversion of furfural that is formed during the dehydration of a hexose.

7. The process according to claim 1, wherein the furan of formula (I) is reacted with the olefin of formula (II) at a temperature of from 0 to 150° C.

8. The process according to claim 1, wherein the furan of formula (I) is reacted with the olefin of formula (II) in the presence of a Lewis acid that is used as a Diels-Alder catalyst.

9. The process according to claim 1, wherein the molar ratio between the amount of furan of formula (I) to the amount of olefin of formula (II) ranges from 0.1:1 to 10:1.

10. The process according to claim 1, wherein the bicyclic ether is dehydrated in the presence of a solvent.

11. The process according to claim 10, wherein the solvent is selected from the group consisting of alcohols, esters, ketones, amides, aldehydes, ethers, ionic liquids and sulphoxides.

12. The process according to claim 10, wherein the solvent is an aliphatic alcohol with 1 to 3 carbon atoms.

13. The process according to claim 1, wherein the catalyst is a basic catalyst.

14. The process according to claim 1, wherein the basic catalyst is selected from the group consisting of alkali metal hydroxides, alkanolates, carboxylates and carbonates.

15. The process according to claim 1, wherein the bicyclic ether is dehydrated at a pressure ranging from 0.5 to 50 bar.

16. The process according to claim 1, wherein bicyclic ether is dehydrated in a batch or continuous reactor wherein the residence time is from 0.1 to 48 hours.

17. The process according to claim 1 wherein the reaction of the furan of formula (I) with the olefin of formula (II) and the dehydration reaction are performed in one step.

18. The process according to claim 1, wherein the oxidation is effected by an oxygen-containing gas in the presence of a catalyst comprising cobalt and manganese or by potassium permanganate or nitric acid.

19. The process according to claim 18, wherein the catalyst comprises cobalt and manganese, and further comprises bromine.

20. The process according to claim 1, wherein the oxidation is carried out at a temperature of from 60 to 220° C., at a pressure of from 5 to 100 bar and at a residence time of from 0.1 to 48 hours.

* * * * *

UNITED STATES PATENT AND TRADEMARK OFFICE
CERTIFICATE OF CORRECTION

PATENT NO. : 9,162,960 B2  
APPLICATION NO. : 14/346380  
DATED : October 20, 2015  
INVENTOR(S) : Matheus Adrianus Dam et al.

Page 1 of 1

It is certified that error appears in the above-identified patent and that said Letters Patent is hereby corrected as shown below:

On the title page of the patent, please add the following Assignee below "Furanix Technolgies B.V." as follows:

Stichting Dienst Landbouwkunding Onderzoek, Wageningen, (NL)

Signed and Sealed this
Twenty-eighth Day of June, 2016

Michelle K. Lee
*Director of the United States Patent and Trademark Office*